United States Patent [19]

Kovacevic

[11] Patent Number: 5,170,663
[45] Date of Patent: Dec. 15, 1992

[54] GRIP SENSOR

[75] Inventor: Nebosa Kovacevic, Plymouth, Minn.

[73] Assignee: N. K. Biotechnical Engineering Company, Minneapolis, Minn.

[21] Appl. No.: 592,509

[22] Filed: Oct. 3, 1990

[51] Int. Cl.[5] ............................................. A61B 5/22
[52] U.S. Cl. ................................... 73/379; 73/862.633
[58] Field of Search ................ 73/862.54, 862.65, 379; 177/211, 229

[56] References Cited

U.S. PATENT DOCUMENTS

| | | | |
|---|---|---|---|
| 1,796,216 | 3/1931 | Pettersson. | |
| 2,708,367 | 5/1955 | Lusk | 73/379 |
| 3,439,761 | 4/1969 | Laimins | 73/862.65 X |
| 4,364,280 | 12/1982 | Kutsay | 73/862.66 |
| 4,674,330 | 6/1987 | Ellis | 73/379 |
| 4,718,287 | 1/1988 | Mishliborsky | 73/862.65 |

FOREIGN PATENT DOCUMENTS 2332764  1/1974  Fed. Rep. of Germany ... 73/862.65

Primary Examiner—Reinhard J. Eisenzopf
Assistant Examiner—E. Shopbell
Attorney, Agent, or Firm—Kinney & Lange

[57] ABSTRACT

A dynamic grip sensor is formed from a unitary block having upper and lower covers. The sensor, being of a size so that it can be gripped by a human hand, comprises two sets of parallel flexure beams connected between outer end blocks and a center block and are loaded by a base plate connected to the outer end block and extending between the end blocks. The flexure beams deflect to respond to hand grip strength. Strain sensors located on the flexure beams and connected in a wheatstone bridge provide indication of gripping strength. The grip sensor may operate apart from a supporting structure or be incorporated into a handle or similar structure.

6 Claims, 2 Drawing Sheets

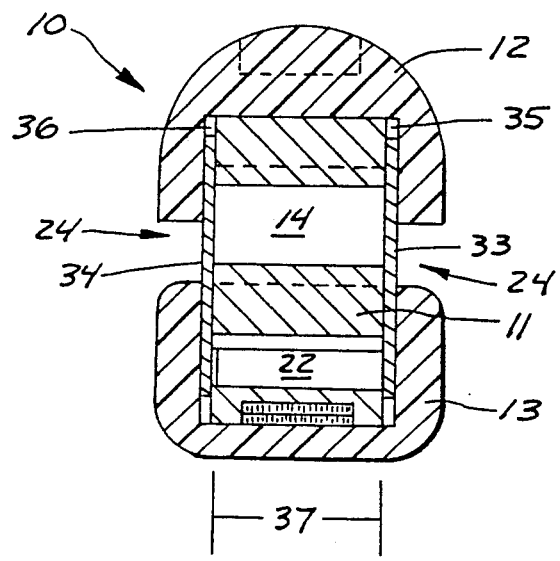
FIG. 5
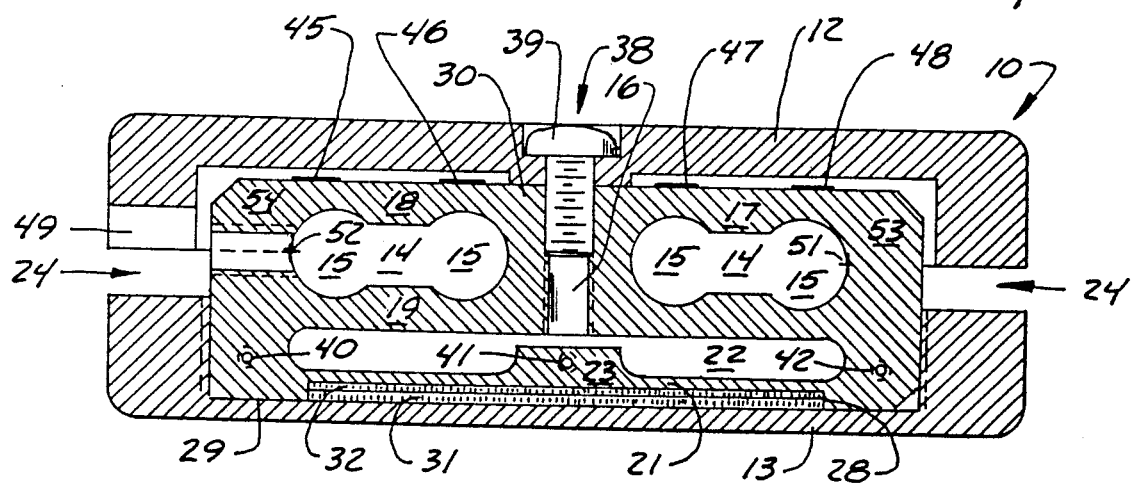
FIG. 6
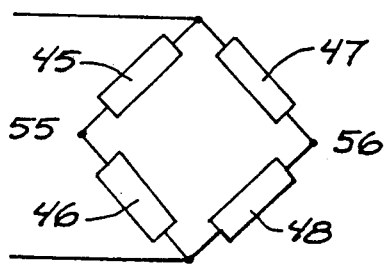

GRIP SENSOR

BACKGROUND OF THE INVENTION

The present invention relates to a one piece structural body with mechanical sensing elements. The sensing elements, designed as flexures, work in connection with strain gauges to provide an accurate hand grip force sensor. Since the grip sensor is light and compact, the grip sensor can be applied to the hand grips of tools and equipment to determine whether the operating forces exerted by the user's hands are within desirable limits.

In the prior art, various grip sensors and pinch sensors have been advanced. For example the sensor shown in U.S. Pat. No. 4,674,330 comprises two parallel handles mounted at one end to a third member. Strain gauges attached to the third member respond in proportion to grip strength when the third member is deflected. However, since the handles are attached only at one end, the third member and thus the strain gauges respond to twisting forces. The net effect is realization of false grip strength measurements. The present invention overcomes this deficiency by using a unitary block of material and incorporating a wheatstone bridge sensor arrangement that cancels out torsion strains developed during testing.

U.S. Pat. No. 1,796,216 teaches a hand held apparatus used for hand muscle development. The apparatus has two spring loaded parts that are gripped and can be clamped together, as well as individual operators for exercising the fingers. The exerciser does not provide for a true readout of forces being generated, nor does it provide parameters for testing a human hand. Therefore, the exerciser is not useful in diagnosing the forces required to operate machines and tools.

Other grip type devices incorporating hydraulic actuation or spring operation have been in use, but these devices are quite large and therefore difficult to use or incorporate for sensing loads on hand held items such as hand tools.

SUMMARY OF THE INVENTION

The present invention relates to a one-piece structural body used as a grasp or grip sensor. The grip sensor comprises a unitary block of material with size and shape to be gripped by the human hand. Upper and lower cover members attach to the block and function as hand grips.

The unitary block functions as a sensing element. A plurality of cross bores define flexure beams and a base plate within the block. Tension and compression strain gauges cooperate with the flexure beams to indicate grip strength exerted on the grip sensor. The strain gauges are connected in a wheatstone bridge to compensate for torsional bending moments developed when the grip sensor is gripped.

The grip sensor measures gripping strength by responding to forces exerted on the upper and lower cover members. Bending moments developed within the unitary block cause flexure beams to deform. The strain sensors respond to beam deformation and thus gripping force.

The grip sensor is compact and easy to use. Due to its lightweight configuration, it can be used singularly to monitor a single hand or in combination with a second grip sensor of the invention to make hand strength comparisons. Furthermore, the grip sensor can be incorporated onto physical objects such as tools to determine required gripping forces.

BRIEF DESCRIPTION OF THE DRAWINGS

FIG. 4 is a sectional view taken along line 4—4 in FIG. 2;

FIG. 5 is a longitudinal sectional view of the block taken along line 5—5 in FIG. 3; and FIG. 6 is a schematic drawing of the strain gauge connections.

DETAILED DESCRIPTION OF THE PREFERRED EMBODIMENTS

Figure 1:
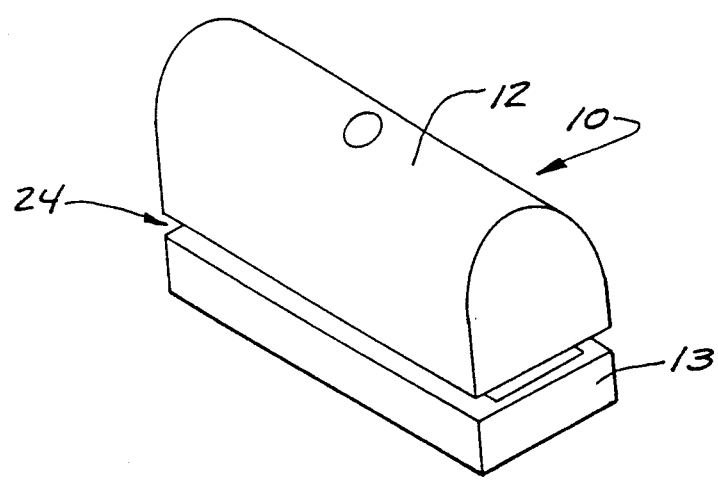
FIG. 1 is a perspective view of a dynamic grip sensor made according to the present invention.
Figure 2:
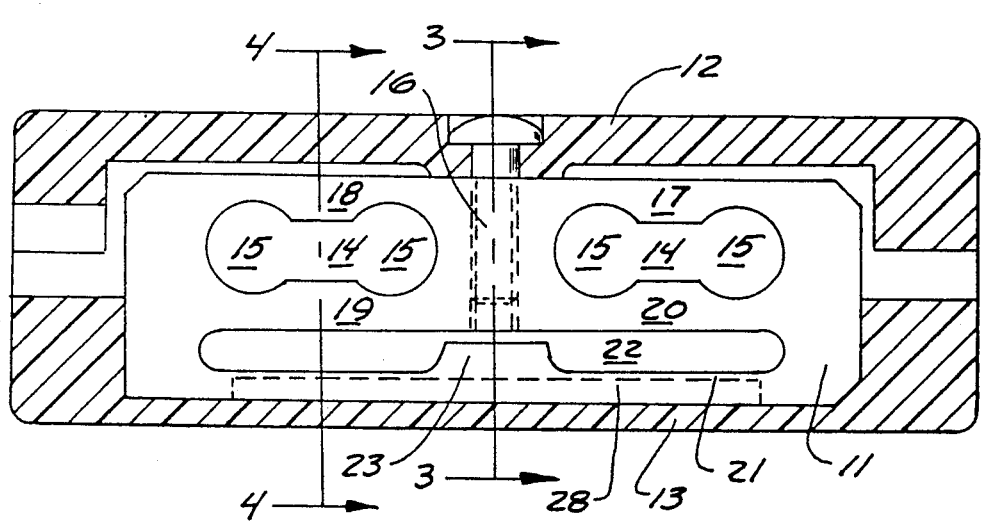
FIG. 2 is a longitudinal side elevational view of the sensing block with the handle grips shown in cross section.

A grip sensor, indicated generally at 10 in FIG. 1 comprises a self-contained flexing block portion 11 (FIG. 2). Block 11 is covered with an upper cover member 12 and a lower cover member 13. The lower cover 13 member is removably held in place onto the main sensing block as will be shown, using Velcro strips or other suitable types of attachment devices. The cover members 12 and 13 function as hand grips and have rounded edges and are constructed so as not to injure a user's hands.

Referring to FIG. 2, block 11 includes structure which deflects under load and is constructed of a unitary block of material. Cross opening 14 and cross bores 15 are cut laterally through block 11 along width 37 (FIG. 4), on opposite sides of a center block 16, to form flexure beams 17, 18, 19 and 20. The larger diameter bores 15 form flex hinge sections at the opposite ends of the beams 17, 18, 19 and 20. These beams act as parallel links when the sensor is loaded.

As shown in FIG. 2, an additional flexible member or base plate 21 is also constructed in block 11. Base plate 21, located below center block 16 and cross opening 14 and bores 15, is created via cross bore 22. A center boss 23, integrally formed on base plate 21, protrudes into slot 22 and acts as a stop when the covers 11 and 12 are gripped and forced together.

Figure 3:
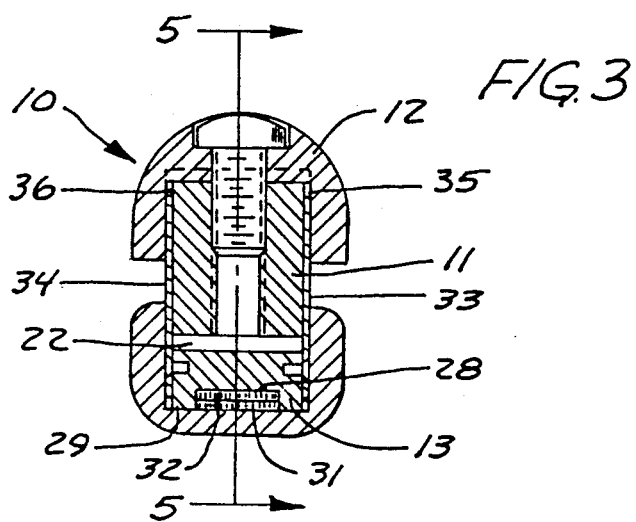
FIG. 3 is a sectional view taken along line 3—3 in FIG. 2.

All principle parts of grip sensor 10 are secured to block 11. As shown in cross section in FIGS. 3 and 5, the upper cover member 12 is held in place on upper surface 30 with a suitable screw 38 that threads into the center block 16. Screw head 39 is recessed within upper cover 12 to prevent contact with the user's hand.

Referring to FIG. 5, lower cover member 13 is secured to block 11 through a hook and loop or Velcro fastener 31 and 32. Velcro strip 31, mounted on lower surface 29 of lower cover 13, locks with Velcro strip 32 located in recess 28 of block 11. Side shield plates 33 and 34 are mounted to both sides of block 11 at points 40, 41 and 42. Gaps 35 and 36 above side shields 33 and 34, shown in FIG. 4, and circumferential gap 24 allow side shields 33 and 34, and cover members 12 and 13, respectively, to move when sensor 10 is gripped and deflection occurs.

Referring again to FIG. 5, strain sensors 45, 46, 47 and 48, located on the upper surface 30, directly measure grip strength exerted on grip sensor 10. The strain gauges are electrically connected in a wheatstone bridge, shown in FIG. 6, to compensate for torsional bending moments developed when the grip sensor is grasped. Conductors connecting the strain sensors enter block 11 through aperture 49.

The grip sensor measures the gripping strength of a hand as follows. The grip sensor is placed in one's hand with the fingers resting on the bottom surface of the lower cover member 13 while the upper cover member 12 makes contact with the palm of the hand. As the hand is closed, upper cover 12 and lower cover 13 are forced together thereby closing gap 24. Meanwhile, base plate 21 deforms as center boss 23 is generally forced upward toward center block 16. The loads on block 16 and reaction on base plate 21 cause the load to be carried through the flexure beams 17, 18, 19 and 20, because of hinge-like flexing connections at the ends of the beams 17, 18, 19 and 20 formed by cross bores 15. Bending moment with axes generally at 51 and 52, direct block portion ends 53 and 54 downward toward each other, while the center pairs of flexure beams 17, 18, 19 and 20 move upward.

Two independent reactions are recorded with strain sensors 45, 46, 47 and 48. Strain sensors 45 and 48 measure the tension strain. Strain sensors 46 and 47 measure compression. With tension and compression strain measuring resistors forming opposite branches of a wheatstone bridge connection as shown in FIG. 6, the gripping force exerted is obtained across bridge terminals or junctions 55 and 56. Furthermore, connection of strain gauges in a wheatstone bridge provides cancellation of extraneous signals caused by twisting or torsion bending about center block 16.

In summary, the grip sensor accurately tests physical parameters such as grip strength of the human hand. The grip sensor can be used singularly to measure a specific hand or in conjunction with another grip sensor to make left/right hand strength comparisons. The sensor's compact and lightweight construction allows it to be incorporated onto physical objects such as tools while combining the grip sensor with a computer and appropriate software provides complete "ergonomic" hand analysis.

Although the present invention has been described with reference to preferred embodiments, workers skilled in the art will recognize that changes may be made in form and detail without departing from the spirit and scope of the invention.

What is claimed is:

1. A grip sensor comprising:
   a unitary block of material being of size so that it can be gripped by a human hand, said block having an upper surface, a center portion and opposite outer ends, wherein said block includes a slot defining a base plate integrally connected to each of the outer ends and spaced apart from the center portion, and cross bores defining a separate pair of spaced, parallel flexure beams between the center portion and each of the outer ends, the parallel flexure beams coupled to the center portion and the respective outer ends through integral flexible hinge sections;
   a stop member acting between the center portion and the base plate to limit movement of the base plate toward the center portion;
   an upper hand grip cover member connected to the center portion of the upper surface of the block, the upper hand grip cover member spaced apart from the upper surface above the parallel flexure beams and the outer ends; and
   means on at least one flexure beam for determining the forces generated by a person gripping the block.

2. The apparatus of claim 1 wherein the stop member is a protruding center boss connected to the base plate below the center portion.

3. The apparatus of claim 1 and a lower hand grip cover member attached to the base plate of the block.

4. The apparatus of claim 3 wherein the lower hand grip cover member is attached to the base plate of the block with Velcro hook and loop fastener means.

5. The apparatus of claim 1 wherein the means for determining the forces generated by a person gripping the block includes means for compensating the torsion bending forces generated about the center portion.

6. The apparatus of claim 5 wherein the means for determining the forces are strain sensors and the means for compensating for torsion bending forces is connection of the strain sensors in a wheatstone bridge.

* * * * *

UNITED STATES PATENT AND TRADEMARK OFFICE
CERTIFICATE OF CORRECTION

PATENT NO. : 5,170,663
DATED : December 15, 1992
INVENTOR(S) : NEBOJSA KOVACEVIC It is certified that error appears in the above-identified patent and that said Letters Patent is hereby corrected as shown below:

```
On the title page, item [75], delete "Nebosa",
  insert "Nebojsa"

Col. 4, line 37, after "compensating", delete "the",
  insert "for"
```

Signed and Sealed this

Nineteenth Day of October, 1993

*Attest:*

BRUCE LEHMAN

*Attesting Officer*     *Commissioner of Patents and Trademarks*